United States Patent [19]

Kaye et al.

[11] Patent Number: 5,471,299
[45] Date of Patent: Nov. 28, 1995

[54] APPARATUS AND METHOD FOR THE ANALYSIS OF PARTICLE CHARACTERISTICS USING MONOTONICALLY SCATTERED LIGHT

[75] Inventors: Paul H. Kaye, Kimpton; Edwin Hirst, Hemel Hempstead, both of Great Britain

[73] Assignee: The Secretary of State for Defence in Her Britannic Majesty's Government of the United Kingdom of Great Britain and Northern Ireland, London, England

[21] Appl. No.: 256,983

[22] PCT Filed: Feb. 18, 1993

[86] PCT No.: PCT/GB93/00337

§ 371 Date: Jul. 29, 1994

§ 102(e) Date: Jul. 29, 1994

[87] PCT Pub. No.: WO93/17322

PCT Pub. Date: Sep. 2, 1993

[30] Foreign Application Priority Data

Feb. 21, 1992 [GB] United Kingdom .................. 9203799
Jan. 13, 1993 [GB] United Kingdom .................. 9300527

[51] Int. Cl.$^6$ .................................................. G01N 15/02
[52] U.S. Cl. .......................... 356/336; 356/338; 356/341; 356/343
[58] Field of Search .................................. 356/336–338, 356/340–343

[56] References Cited

U.S. PATENT DOCUMENTS

| | | | |
|---|---|---|---|
| 4,273,443 | 6/1981 | Hogg | 356/343 |
| 4,341,471 | 7/1982 | Hogg et al. | 356/343 |
| 4,606,636 | 8/1986 | Monin et al. | 356/338 |
| 4,943,159 | 7/1990 | Oetliker et al. | 356/338 |
| 5,043,591 | 8/1991 | Ludlow et al. | 356/343 |
| 5,089,714 | 2/1992 | Ludlow et al. | 356/343 |
| 5,127,729 | 7/1992 | Oetliker et al. | 356/338 |

FOREIGN PATENT DOCUMENTS

| | | |
|---|---|---|
| 0098095 | 1/1984 | European Pat. Off. . |
| 0391682 | 10/1990 | European Pat. Off. . |

*Primary Examiner*—Richard A. Rosenberger
*Assistant Examiner*—Jason D. Eisenberg
*Attorney, Agent, or Firm*—Nixon & Vanderhye

[57] ABSTRACT

An apparatus for the analysis of individual particle characteristics from an aerosol or other suspension of particles, of the type having a scattering chamber (15) with an ellipsoidal reflector (17) and an orifice leading to a rear chamber (20), and a monochromatic light source (10) adapted to transmit a collimated beam of light (11) along the main axis of the reflector (17) to impinge on a stream of the particles reflector (17), has an optical system (17, 32, 33, 34) arranged to collect light back-scattered from a particle, through a solid angle of at least 3π, pass the light to a a ccd video recorder (36) having a two dimensional array of a multitude of sensors.

The recorder (36) is associated with a data processor (37) and with an imaging screen (35) positioned such that rays of light scattered from the particle and imaged thereon by the optical system (17, 32, 33, 34) are monotonically ordered with respect to the angle of scattering of the rays from the particle.

18 Claims, 6 Drawing Sheets

APPARATUS AND METHOD FOR THE ANALYSIS OF PARTICLE CHARACTERISTICS USING MONOTONICALLY SCATTERED LIGHT

BACKGROUND OF THE INVENTION

1. Field of the Invention

The ability to measure particles by shape and size is of importance to many groups of people. The food and chemical industries are concerned from a quality control point of view; biologists are interested in characterising cells and monitoring changes in and differences between cells; environmental scientists are concerned with airborne particles and their effect on air quality and health. This list is by no means exhaustive, it is merely intended to illustrate the driving force behind the attempts to develop accurate and reliable measurement instrumentation, and to theoretically understand the nature of the problem.

2. Discussion of Prior Art

There are currently two main optical scattering methods in use in commercially available particle measurement systems. The first method attempts to size particles by measuring their static or dynamic behaviour in fluid. These systems generally measure deposition rate, acceleration in a let stream, or Brownian motion. The second method attempts to size particles by measuring the light scattered from an illuminated particle or ensemble of particles either at a few specific angles or over a large solid angular range. Apart from image analysis systems, none of the commercial instruments is capable of characterising particles by shape, non-spherical particles being sized by assigning an equivalent spherical diameter, although this diameter depends on the measurement method used. What is worse, is that some instruments are known to become inaccurate when tested with non-spherical particles of regular shape, so measurements taken with particles of arbitrary shape have to be treated with some caution.

Instruments which attempt a shape classification are based on image analysis, which requires taking an image of a small number of particles and performing complex image processing. The particle sample has to be prepared beforehand so that it is in a form suitable for image processing, i.e. it has to be processed so that individual particles can be seen with minimal overlapping. Thus there is a considerable time delay before the results are available. The method also requires fast computers in order to do the analysis reasonably quickly. Some of the other instruments also suffer a time delay before measurements are available, and whether this is important depends on the application. It is not necessarily important for batch testing powders for example, but it is of potential importance when monitoring a working environment for asbestos fibres or micro-organisms.

Several commercial laser based instruments are available which will size particles, as disclosed in "Particle Size Analysers Product Roundup", Powder and Bulk Engineering, Feb 1991; pp 42, and other research instruments have been built to investigate various aspects of particle sizing. For example, an instrument has been developed to size particles using the oscillation in intensity of the scattered light, as disclosed in "Drop Sizing by Laser Light Scattering Exploiting Intensity Angular Oscillation in the Mie Regime" by Ragucci, R., Cavaliere, A. and Massoli, P. Particle and Particle Systems Characterisation, Vol 7, 1990; pp 221. Most of the instruments analyze an ensemble of particles and, as stated previously, they assume a spherical particle or particles, and do not give any indication of non-sphericity.

Research reported in "Light Scattering Instrument to Discriminate and Size Fibres Part 2: Experimental System". Particle and Particle Systems Characterisation, Vol 6, 1989; pp 144, has been reported using an instrument designed to discriminate and size fibrous material. In this research, particles are passed through a laser beam in single file using a laminar airflow system similar to the design described below. The forward scattered light is collected by a lens and passed through a polarizing beamsplitter. The intensity of the light in two orthogonal polarizations is then recorded using photo-multiplier tubes. Results show that near spherical particles can be discriminated from fibrous particles by taking the ratio of the polarized intensities, provided that the particle diameter is above 1.5 microns approximately.

An instrument which has been developed to size particles uses the laser Doppler velocimetry technique of "Strengths and limitations of the phase Doppler technique for simultaneous measurements particle velocity and size." by Livesley, D. M. Proceedings-SPIE International Society for Optical Engineering Vol 952, 1988; pp 454, and this has also shown a capability of discriminating near spherical particles from fibrous ones. This technique is based on refraction of rays by the particle, so it is limited to particles larger than 5 microns. The instrument uses two coherent laser beams which interfere with each other, creating a series of fringes in the scattering volume. The spacing of the fringes depends on the wavelength of the lasers and the angle between the beams. Three photo-multiplier tubes are used at different angles of forward scatter which together give an indication of particle speed, size, and non-sphericity. The speed is obtained from the time it takes the particle to traverse from one fringe to the next. The size is obtained from the phase difference in the signals from two detectors, which is a function of speed and particle surface convexity, the rate of sweep of the refracted ray as the particle traverses the fringe being larger for a smaller particle. The third detector allows a second phase difference to be measured, and a difference in the two measured phases is seen when the particles are non-spherical.

We have disclosed in "An instrument for the classification of airborne particles on the basis of size, shape, and count frequency." Atmospheric Environment, Vol 25A No. 3/4, 1991; pp 645 by Kaye, P. H., Eyles, N. A., Ludlow, I. K., and Clark, J. M., and in Applications EP-A-0316171 and EP-A-0316172 an airborne particle classifier (APC) which has some capability of determining particle shape as well as size: it is shown in FIG. 1 of the accompanying drawings and described in detail below. The system is capable of collecting information on a maximum of 10,000 particles per second, and is thus capable of quasi-real time operation. However, the shape information is severely limited because of the small number of detectors, and it is unlikely that it could be used to differentiate unambiguously between different types of non-spherical particle, e.g. fibres and platelets. There is also uncertainty in the trajectory and orientation of particles as they pass through the beam, and it is difficult to determine and allow for the effect of these on the scattering with only three detectors.

US-A-4606636 describes an arrangement where a flow stream carrying particles is carried in a transparent capillary tube along the axis of a non-divergent quadric reflector. A beam of light intercepts the tube at the focus of the reflector, non-reflected scattered rays are intercepted and reflected scattered rays are received on a photosensitive cell or optical scanner which feeds a processing system.

All these prior art systems using quadric reflectors operate on the assumption that the light beam will impinge on a particle at the focus of the reflector. In practice, this is not true. In practice the flow stream will always have a finite thickness and particles carried thereby will not always cross the focus of the reflector. This results in variations of ray path which can result in rays becoming non-monotonic (that is rays scattered at low angles and reflected cross those scattered at higher angles) before being recorded. Images from monotonic and non-monotonic rays are completely different.

Thus no real-time method of shape analysis is yet available, and little investigative work has been done on non-spherical particles.

SUMMARY OF THE INVENTION

According to the present invention apparatus for the analysis of individual particle characteristics from an aerosol or other suspension of particles includes: a scattering chamber including an optical system having an ellipsoidal reflector with an orifice therein leading to a rear chamber;

a monochromatic light source adapted to transmit a collimated beam of light along the main axis of the reflector;

means for directing a gas stream of finite thickness containing particles through the beam of light at substantially a main focus of the reflector;

the optical system being arranged to collect the scattered light from a solid angle of at least $3\pi$ around the region where the particle stream crosses the light beam;

a detector having a two dimensional array of a multitude of sensors arranged to form an image from light scattered from a particle in the stream of particles and collected by the optical system;

and a data processor, the data processor being adapted to compare parameters of the image with parameters stored in a memory to determine the nature of the particle;

characterised in that the recorder is associated with an imaging screen positioned behind a secondary focus of the reflector such that, whatever part of the finite thickness of the gas stream occupied by the particle when it passes through the beam of light, rays of light scattered from the particle and imaged thereon by the optical system are monotonically ordered with respect to the angle of scattering of the rays from the particle so that the image recorded on the imaging screen is substantially independent of the position of the particle in the gas stream.

The detector is preferably a charged couple device (ccd) video recorder.

The imaging screen may be an image intensifier or the image screen of the camera.

The apparatus might advantageously include trigger means, which might have sensor means for sensing scattered light not collected by the optical system, and thereby determining the presence of a particle in the beam of light, and for triggering the detector to store the image associated with the particle. The sensor means might comprise a photomultiplier tube onto which are focussed scattered rays which pass through the orifice in the optical system to the rear chamber.

In instruments including a photomultiplier provision might be made for changing the positions of photomultiplier and detector, or even replacing the photomultiplier with another detector.

The trigger means might also include a controller having an input from the detector means and an output to the detector, and might be adapted to act only with a single particle in the beam.

The parameters compared might relate to entire images, to parts of images, or to resolving diffraction or interference maxima and minima.

According to another aspect of the invention a method of analysing individual particle characteristics from an aerosol or other suspension of particles includes the steps of directing a gas stream of finite thickness containing particles through a scattering chamber;

the scattering chamber including an optical system having an ellipsoidal reflector with an orifice therein leading to a rear chamber;

a monochromatic light source adapted to transmit a collimated beam of light along the main axis of the reflector;

means for directing the gas stream through the beam of light at substantially the main focus of the reflector;

the optical system being arranged to collect the scattered light from a solid angle of at least $3\pi$ around the region where the particle stream crosses the light beam;

the scattering chamber being associated with a ccd video recorder having a two dimensional array of a multitude of sensors arranged to form an image from light scattered from a particle in the stream of particles and collected by the optical system;

the video recorder passing information to a data processor, the data processor being adapted to compare parameters of the image with parameters stored in a memory to determine the nature of the particle;

characterised in that the recorder is associated with an imaging screen positioned behind the secondary focus of the reflector such that, whatever part of the finite thickness of the gas stream occupied by the particle when it passes through the beam of light, rays of light scattered from the particle and imaged thereon by the optical system are monotonically ordered with respect to the angle of scattering of the rays from the particle so that the image recorded on the imaging screen is substantially independent of the position of the particle in the gas stream.

Preferred embodiments of the invention are intended to be capable of classifying particles into one of five broad shape classifications: spheres, droplets, fibres, platelets and "chunks" (i.e. particles of comparable size in all three dimensions), and also of differentiating between particles of differing aspect ratio.

In this specification, the term "scattering profile" is intended to mean the three-dimensional scattered light intensity distribution about the particle. The scattering profile is unique for particles of given shape, orientation, and dielectric structure for a given wavelength of illumination.

BRIEF DESCRIPTION OF THE DRAWINGS

In order that the invention may be better understood, an example will now be described in detail with reference to the accompanying drawings, in which.

DETAILED DISCUSSION OF PREFERRED EMBODIMENTS

Figure 1A:
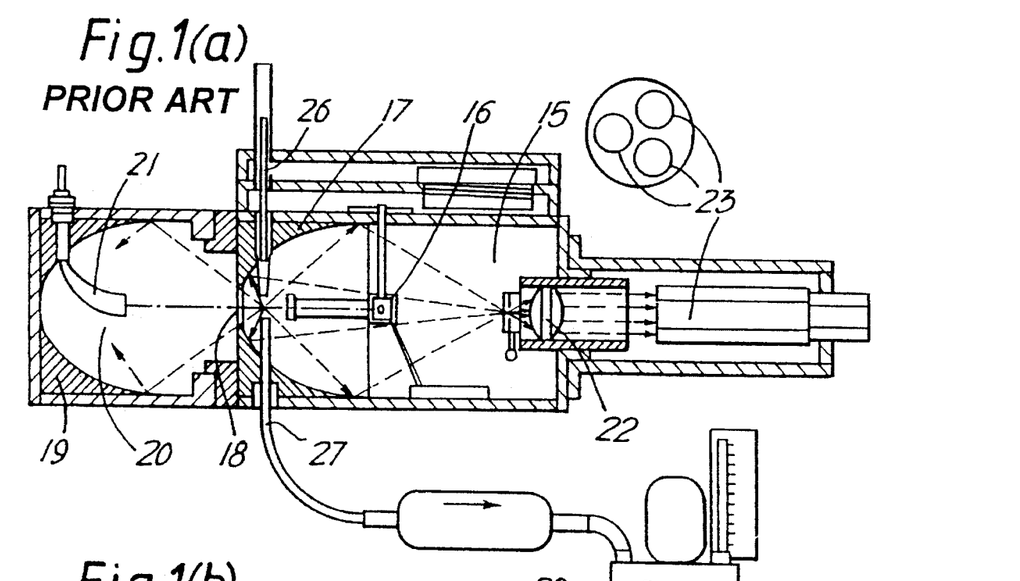
FIG. 1a, to which reference has already been made, is an elevation of a conventional particle analysis instrument.
Figure 1B:
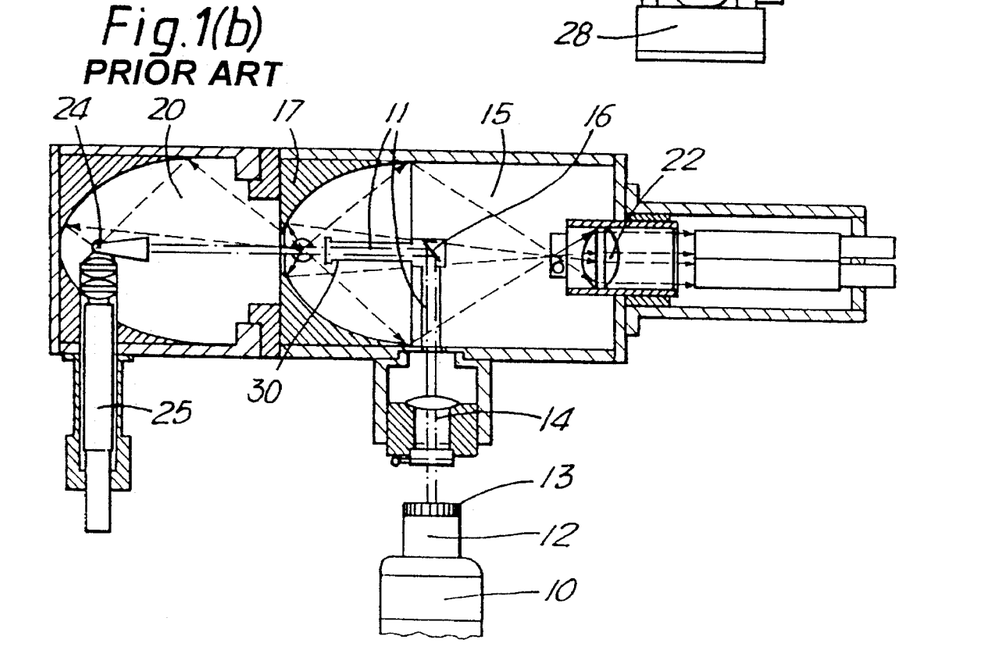
FIG. 1b is a corresponding plan view.

The prior art device illustrated in FIGS. 1a and 1b, as described in EPA 0316172, has a laser 10, for example a HeNe laser., projecting a beam 11 through a beam expander 12, iris diaphragm 13 and cylindrical lens 14 at right angles into a scattering chamber 15. In the scattering chamber 15 the beam 11 is reflected by a mirror 16 to pass through a shroud 30 along the axis of a first ellipsoidal reflector 17, positioned in the main chamber 15, through an orifice 18, along the axis of a second ellipsoidal reflector 19 in a reap chamber 20 and through a beam dump 21. At the rear of the scattering chamber 15 is a collimating lens 22 and a collection system comprising three photo-multiplyer tubes 23. At the focal point of the second ellipsoidal reflector 19 in the rear chamber 20 is a radiation collector 24 leading to a photomultiplier lens 25. A sample inlet tube 26 and sample outlet tube 27 are positioned in the scattering chamber 15 such that a sample of gas can be passed through the focal point of the first ellipsoidal reflector 17.

In use a sample is drawn by a pump 28 through the tubes 26, 27, such that particles therein are illuminated by the beam 11. Light deflected by the particles through a substantial angle ape reflected by the first ellipsoidal reflector 17 and pass through the collimating lens 22 to the photomultipliers 23. Light deflected at lower angles pass through the orifice 18 into the back chamber 20 where they are reflected by the second ellipsoidal reflector 19 onto the radiation collector 24 and thence to the photomultiplier 25. Non-reflected light is dumped by the beam dump 21.

The outputs of the photo-multiplier tubes are digitized and stored using dedicated electronics and analysed using a computer, for example by comparison with data or with known shapes as described in EP-A-0316171.

Figure 2:
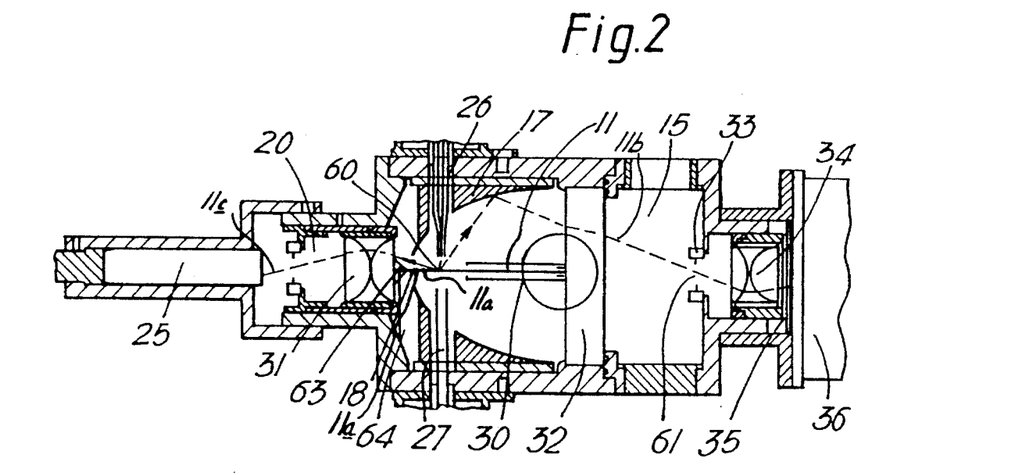
FIG. 2 is a sectional view showing a scattering chamber according to the present invention.

Due to the considerable promise shown with the instrument described with reference to FIG. 1, the new instrument shown in FIGS. 2, 3 and 8 retains the same ellipsoidal reflector light collection system and the same type of particle delivery system. As the present invention relies for its operation on specific positioning of certain items and of calibration it will be described with reference to an actual experimental instrument.

In an instrument according to the present invention (FIG. 2) a laser beam 11 delivered by a laser system similar to that shown in FIGS. 1 is contained initially within a shroud 30 (constructed and mounted as shown in FIG. 1b) and directed along the axis of an ellipsoidal reflector 17 in a scattering chamber 15, through an orifice 18 and then onto a beam dump in the form of a silvered prism 63 glued to a lens of a forward scatter lens assembly 31 and directing unscattered light 11a light onto a matt black surface 64. The lens assembly 31 is adapted to focus scattered light onto a photomultiplier tube 25 in a rear chamber 20. The laser was a Lasermax model LAS-200-670-10 diode module with integral power supply and collimating optics. This laser has a power output of 10 mW at a wavelength of 670 nm. The output is plane polarized and operates in the $TEM_{00}$ mode, with a cross section of 4 mm by 1 mm. The module was mounted in the housing by set screws which enabled it to be aligned with the chamber. The beam passes through a quarter wave plate to render it circularly polarized, through an iris diaphragm and then through a cylindrical lens before entering the scattering chamber 15. The beam 11 at a main focus 60 of the ellipsoidal reflector 17 was thus approximately elliptical with dimensions 3 mm wide and 120 microns deep. The laser housing could be moved inside the mounting to allow for cylindrical lens focal length tolerances. The ellipsoidal reflector 17 was chosen For its collection capabilities, had the main focus 60 and a secondary focus 61 separated by 98.6 mm, and had a quoted solid angle collection of 84% of the sphere surrounding the main focus 60 ($3.3\pi$ of the $4\pi$ solid angle). A sample inlet tube 26 and sample outlet tube 27 connected to a pump, for example a vane type pump whose output can be adjusted, are arranged to supply a sample stream across the light beam 11 at the main Focus of the ellipsoidal reflector 17. The optical arrangement is such that light scattered by a particle in a sample and being reflected by the ellipsoidal reflector 17, which encompasses a solid angle of at least $3\pi$, passes through an optical window 32 and an iris 33 positioned at the secondary focus of the reflector 17. The optical window 32 increases the distance between the main and secondary Foci of the reflector 17 and the iris 33 reduces the amount of background scatter. From the iris 33 reflected light passes through a pair of plano-convex lenses 34 to an image intensifier 35 positioned adjacent a video camera 36. The camera was a typical charged couple device (ccd) video camera with a 110880 (385 by 288) element array. The position of the image intensifier (or any alternative imaging screen) in the system is critical, as will be discussed below with reference to FIGS. 5 to 8 of the accompanying drawings.

Figure 3:
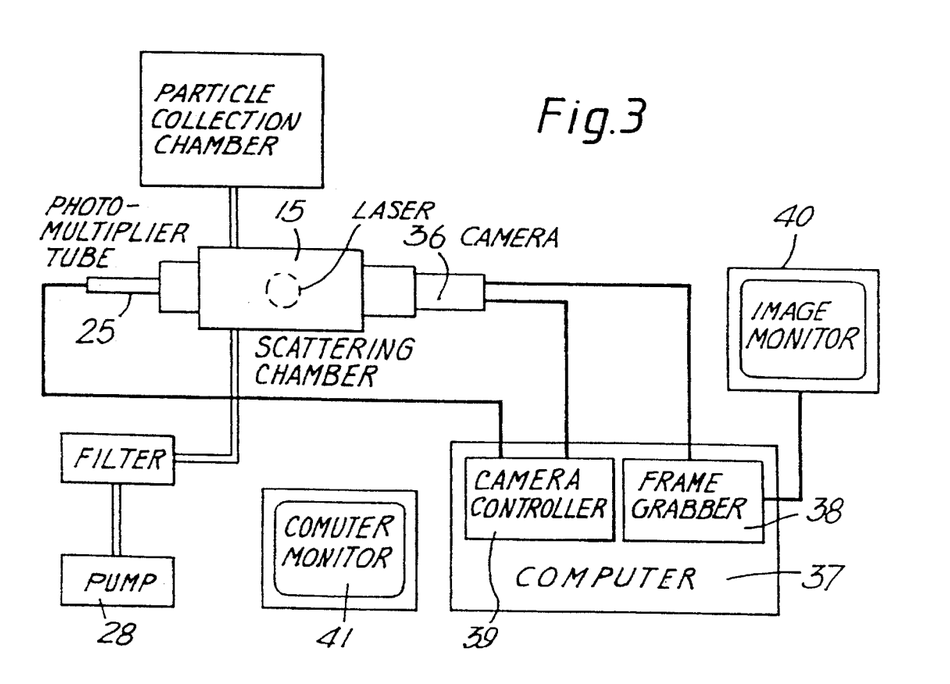
FIG. 3 is a diagrammatic representation of the system of the present invention.

The recording, analysis and viewing arrangements of the invention may best be seen from FIG. 3. A computer 37 contains, inter alia, a frame grabber 38 which has an input from the camera 36 and a camera controller 39 which has an input From the photomultiplier 25 and an output to the camera 36. The frame grabber 38 was a commercial board with a 256 by 256 pixel array, which was available with commercial software For post processing of images. The computer has the normal storage and calculation facilities, and outputs to an image monitor 40 and to a computer monitor 41.

The sample inlet assembly (FIG. 4) including the sample inlet tube 26 has the tube 26 leading from a sheath air chamber 50 to which can be supplied, through a sheath air inlet 51, Filtered air. Co-axial with the inlet tube 26 is a sample air tube 52 leading From a sample chamber 53 to lie within the inlet tube 26 where it terminates adjacent a narrowing 54 in the tube 26. The exact positioning of the termination relative to the narrowing 54 can be adjusted by an adjustment screw 55, and the extension of the sample inlet tube into the scattering chamber 15 can be adjusted by the adjustment screw 55.

Figure 4:
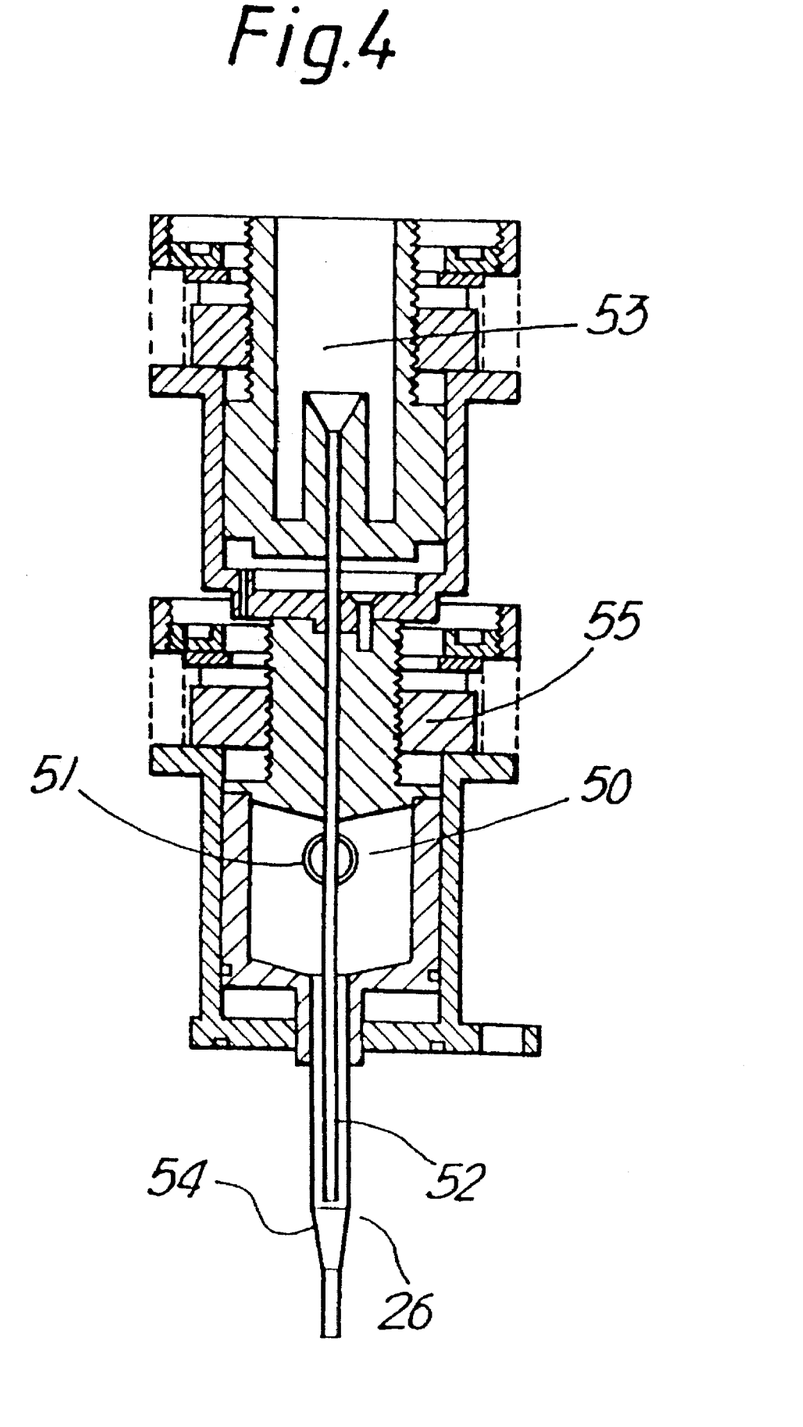
FIG. 4 is a sectional view through the sample inlet assembly.

In use during calibration clean filtered sheath air is delivered via the air inlet 51 and sheath air chamber 50 to the sample inlet tube 26, and sample air, containing particles of a known type is delivered to the sample air tube 52 From the sample chamber 53. Operation of the pump 28 draws sample air, surrounded by a sheath of clean Filtered air, out of the sample inlet tube 26, across the laser beam 11, and into the sample outlet tube 27. The sample air is drawn through the chamber at (2.5–6)l/m creating a columnar, laminated airflow with a diameter of 1 mm across the gap between the tubes. Particles thus pass in single file through the laser beam 11 within 0.5 mm of the main focus 60 of the ellipsoidal reflector. The laser beam 11 impinges on any particle in the sample air at substantially the main Focus 60 of the ellipsoidal reflector 17 and as a result light is scattered. Scattered light 11b impinging on the ellipsoidal reflector 17 is reflected through the optical window 32, iris 33 and lenses 34 onto the image intensifier 35. Scattered light 11c not impinging on the reflector 17 passes through the orifice 18 and forward scatter lens 31 where it is Focussed onto the photomultiplier tube 25. Light not scattered is dumped.

The photomultiplier tube 25 passes a signal to the camera controller 39, which monitors the signal. When a predetermined level is reached a signal is sent to the camera 36 causing the camera to image the pattern on the image intensifier 35 and pass this image to the frame grabber 38 whence it is stored in the computer 37- The image, which is distinctive of the type of particle and (if relevant) of its alignment, may be viewed on the image monitor 40.

Figure 5:
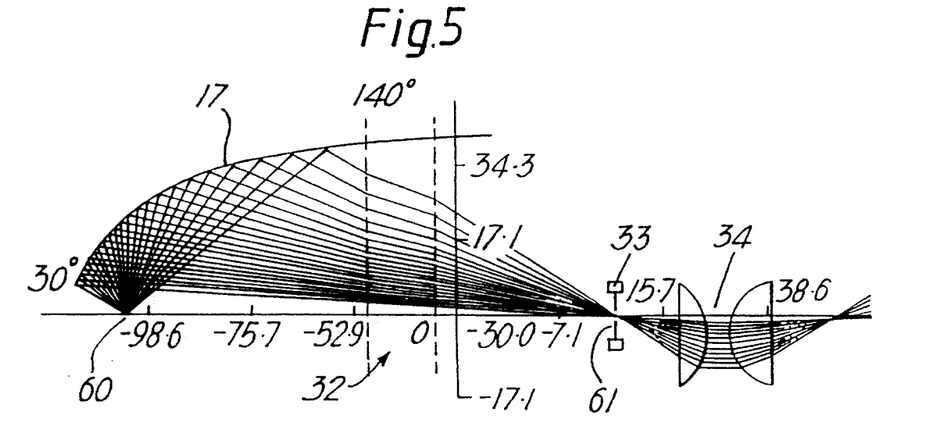
FIGS. 5 to 8 are ray trace diagrams illustrating the passage of light in the scattering chamber.

It will be realised that in practice the sample air stream will have a finite thickness. Particles will not therefore always cross the main focus 60 of the reflector 17 when the laser beam 11 impinges thereon. This is illustrated in FIGS. 5 to 8. In FIG. 5 is shown a ray trace of the complete optical system for the particular ellipsoidal reflector 17, optical window 32, iris 33 and lenses 34. The dimensions are in mm measured from an origin at the secondary focus of the reflector 17 and the traces correspond to scattering angles 30° to 140° in 5° steps.

Figure 6:
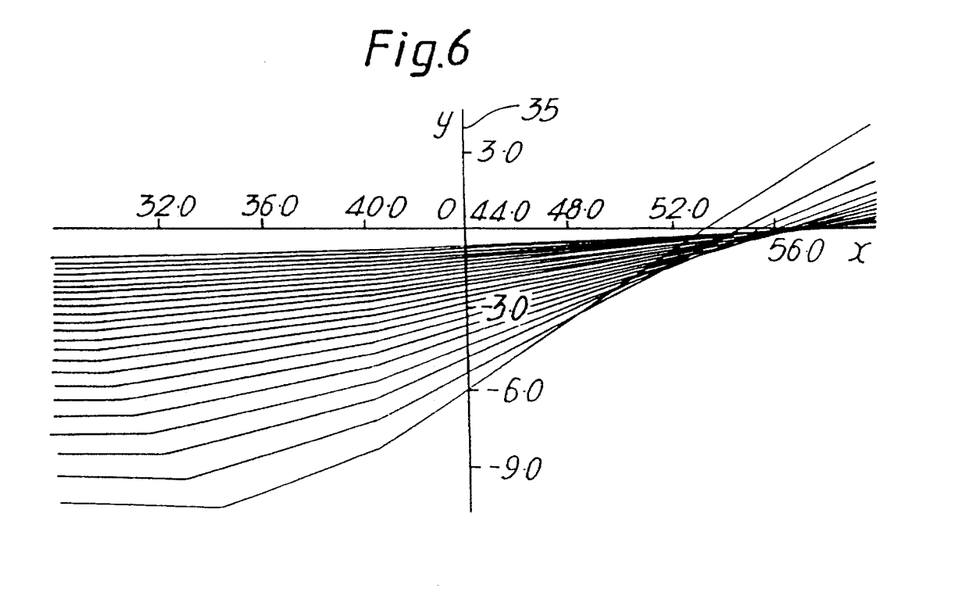

FIG. 6 shows a detail of the ray trace of FIG. 5, in the region of the image intensifier 35 which is shown at a position +44 mm from the origin. It will be seen that at this position the rays are monotonic (that is rays scattered at low angles and reflected do not cross those scattered at higher angles).

Figure 7:
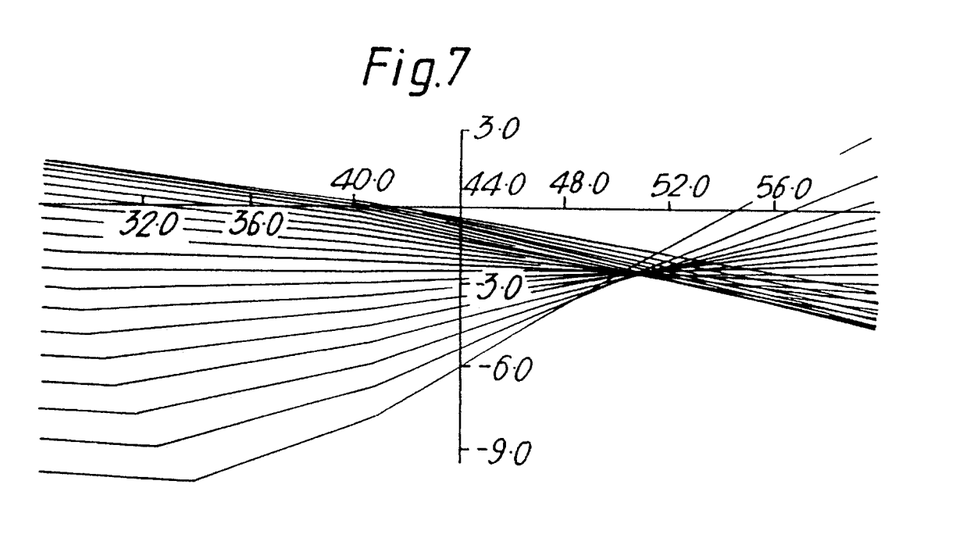
Figure 8:
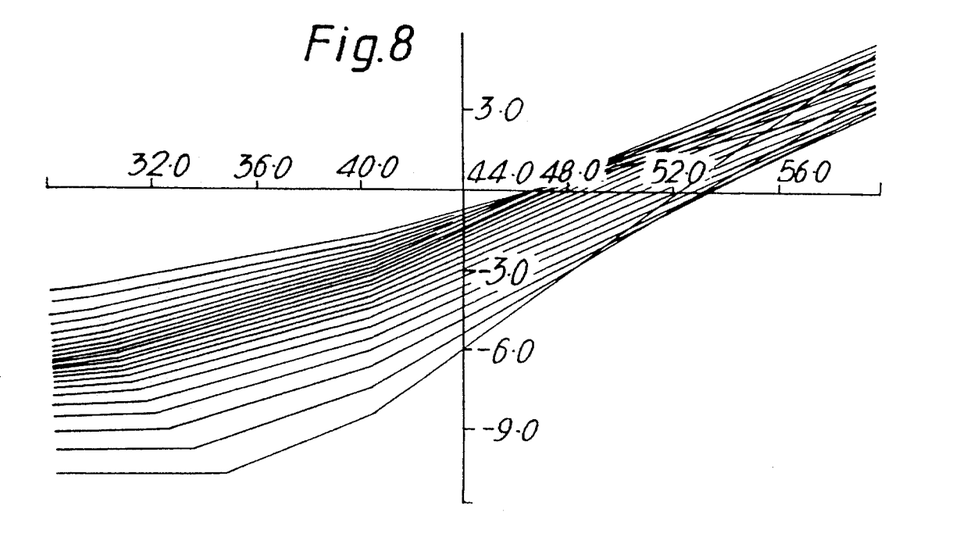

FIGS. 7 and 8 show respectively traces of rays for particles crossing the beam 11 0.5 mm forward (toward the vertex of the reflector 17) and 0.5 mm rearward of the main focus 60 of the reflector 17, and it will be seen that shortly to the left and right of the 44 mm position the rays become non- monotonic, whilst being monotonic at the 44 mm position. Whilst the rays remain monotonic the images presented by a given particle remain substantially identical (other than some degree of distortion) whatever the crossing position of the particle relative to the main focus 60 and can therefore be successfully compared with a memory of that image. However once the rays become non-monotonic the image is completely changed and will not be comparable. It is therefore essential that the image intensifier 35, or other imaging screen, is placed in a position where rays will be monotonic whatever the position a particle crosses the laser beam 11. The optimum position of the image intensifier 35 can be determined by trial and error by passing a stream of particles through the instrument whilst moving the image intensifier 35 to determine the position where complete duplication of images is lost. Alternatively a manouvrable sample inlet tube 26, supplying a very narrow sample jet may be used to test the effects of particles passing at known distances from the main focus 60. It will be realised that using very narrow sample jets such that all particles will cross the laser beam 11 substantially exactly at the main focus 60 of the reflector 17 will provide an instrument that will be too slow acting to be of practical value. For the instrument described here as calibrated for commercial use a sample jet width of about 1 mm would be typical.

It will be realised that, in practice, at times two or more particles will cross the laser beam 11 so closely together that scattered light from both will be imaged unless precautions are taken. This can be avoided by sensing the time during which the camera controller 39 is receiving an intake from the photomultiplier unit 25 and aborting the triggering of a camera action if this time is too great (indicating the presence of more than one particle).

When the position of the image intensifier 35 and the timing of the camera controller have been set the instrument can be calibrated by passing a series of particles of known size, shape and constitution therethrough and storing the images or other parameters (such as diffraction or interference maxima or minima, or details of portions of the image) in a library for future comparison. Once one instrument has been calibrated it can, of course be expected that instruments of similar construction will provide similar results, and the calibration may prove to be suitable for such similarly constructed instruments.

When storing images to hard disc the image capture rate is limited by factors such as the speed limitations of the disc, and fop the system described above might be approximately two images per second.

With the instrument described above, the light scattered between 28° and 141° from a particle was collected by the ellipsoidal reflector 17, (i.e. the scattered light was collected from a solid angle of at least $3\pi$ around the region where the particle stream crosses the beam 11). The reflector 17 was mounted in a cylindrical holder which could be moved to position it correctly. This was necessary because although the optical and mechanical dimensions of the reflector are specified, no relationship between them is given. The light scattered between 5° and 28° from a particle passed to the pair of plano-convex lenses 31.

Compared with the performance of the instrument of FIG. 1 the present invention gives greatly increased spatial resolution. By use of a charge coupled device (ccd) video camera coupled with an image intensifier four advantages are gained:

1. The resolution is increased by replacing three detectors with the 110880 (385 by 288) elements of the ccd array.

2. The light input to charge output conversion efficiency is virtually constant across the array because it is manufactured in one piece of silicon.

3. The light gain of the image intensifier is also virtually constant over its aperture due to its construction.

4. Use of a video camera means that images can be captured on a standard computer frame grabber board, and therefore can be processed and stored faster than with a still camera using photographic film.

The image intensifier is required in this example of the invention because of the small number of photons scattered from a particle during its transit through the laser beam. The time of transit of a particle through the beam is approximately (2–5) microseconds depending on flow rate, during which time typically several thousand photons are scattered depending on particle size, when using a focused 10 mW helium-neon laser as in the instrument. The number of photons scattered depends approximately on the fourth power of the particle size in the size range of interest (approximately 1–10 microns), and hence varies considerably. The camera 36 has an asynchronous trigger facility which allows it to be used in a similar manner to a still camera. This is necessary so that the scattered light can be captured during the time that a particle is in the beam 11.

The maximum number of images that the camera 36 can output is 25 per second, i.e. it can record data on 25 particles per second, as opposed to the data rate of 10,000 particles per second of the original instrument. This is not a disadvantage however, since the instrument in this example is used for basic research into scattering profiles from particles of different shape. The high spatial resolution offered by the camera 36 allows the determination of an optimum detector configuration fop use in Peal time instruments with more rapid particle handling rates, also embodying the invention. Such an optimised detector configuration may well have fewer elements, for example 32 by 32 than a camera CCD array so as to allow a higher particle analysis rate. The configuration need not be symmetrical, and may be optimised to suit analysis of a specific particle shape. Examples would include a custom multi-element photodiode array arranged geometrically for optimum shape characterisation.

In one particle size range of particular interest (1–10 microns), a significant proportion of the total scattered light is scattered in the angular range up to 30°. This light passes through the hole 18 in the ellipsoidal reflector 17, and is thus not collected by the camera 36. Light scattered in this angular range may be of importance in determining particle shape and the instrument is preferably designed so that this angular range could be investigated if necessary.

The light passing through the orifice 18 is normally collected by a photo-multiplier tube 25 which generates a pulse to trigger the camera 36, and when the scattering chamber 15 is designed to allow the camera 36 and photo-multiplier tube 25 housing to be interchanged the arrangement allows the camera 36 to record scattering in either the range 5°–300° or the range 30°–140°.

Previous results recorded from fibres have shown that there could be differences in orientation between particles as they traverse the gap between the inlet and outlet tubes 26, 27. To investigate this more thoroughly the distance between the inlet 26 and outlet 27 tubes was made adjustable, so that the distance between the ends of the tubes and the laser beam could be varied. The depth of the particle delivery tube 52 inside the concentric clean air tube 26 was made adjustable so that the aerodynamic focusing effects of this system could be investigated.

In the original instrument the clean air filter was an integral part of the instrument, which meant that only total airflow could be monitored. In the new example of FIG. 2 it was a requirement that the clean air flow rate could be monitored separately as well as the total, so that the ratio between particle laden air and clean air could be monitored and adjusted.

The camera controller 39 will usually be a purpose-built board acting in a system with a micro-computer which enables the grabbing and storing of frames to be controlled from a keyboard. The computer 37 performs any post processing of the images which may be necessary.

The optical system was designed with the help of a dedicated ray tracing computer program package, so that the effects of particles passing through the scattering volume at different positions could be determined. This was necessary because the ellipsoidal reflector 17 causes the images to be a non-linear representation of the scattering angle, and this in turn is a function of particle position. The design parameters were 1. The total solid angle collected should be as large as possible.

2. The system should be designed to cope with changes in particle position within the scattering volume.

3. The diameter of the projected image on to the camera faceplate should equal to the camera aperture.

The first criterion is best satisfied by collecting the light with an ellipsoidal or parabolic reflector. Criteria 2 and 3 were found by modelling to be satisfied by the condenser lens 34 arrangement. Several different configurations of lenses were modelled on the ray tracing software before arriving at the one shown in FIG. 5 as a suitable solution.

With reference to the frame grabber board 38 this preferably contains in its software an expert system for classifying spatial distributions of the captured video frame diffraction maxima corresponding to known particles of different shapes and sizes, and for then identifying those characteristics in test particles. The analysis may include recording features of the spatial arrangement of the image maxima for each of several particles for whom the relevant characteristics are known, and then using those features to set the predetermined criteria For analysis of test particles.

The camera controller 39 is newly designed to control the camera 36 triggers and frame grabber 38 and has four main functions as follows:

1. Trigger generation. The board uses the output of the photo-multiplier tube to generate two trigger pulses, one for the image intensifier 35 and the other for the video camera 37. The image intensifier 35 is turned on for the duration of time that the particle is in the scattering volume and thus acts as an electronic shutter. The camera trigger pulse is of 3 ms duration and starts after the trigger is removed from the image intensifier. This timing arrangement was found to improve the quality of the images by reducing ccd overspill between elements (smearing). The persistence of the image intensifier phosphor ensures that no data are lost. The trigger pulses can be disabled from the keyboard.

2. Noise floor setting. The level below which the camera 36 will not be triggered can be set from the keyboard. This prevents the camera being falsely triggered by noise from the photo-multiplier tube.

3. Time of flight checking. The board contains a counter which records the length of time that a particle is in the laser beam to a resolution of 125 ns. This can be read from the keyboard or by programs and is used to discriminate between genuine single particles and either particles floating into the beam outside the scattering volume, or two or more particles following each other through the beam. It is not possible to detect if two or more particles pass through the beam alongside each other, unless this is evident from the image generated by the camera.

4. Interrupt generation. The camera has a digital output which signals when it is about to output an image. This is used by the board to generate interrupts at the start and end of the video frame. A software interrupt routine then sets up the frame grabber board to capture the frame.

Figure 9:
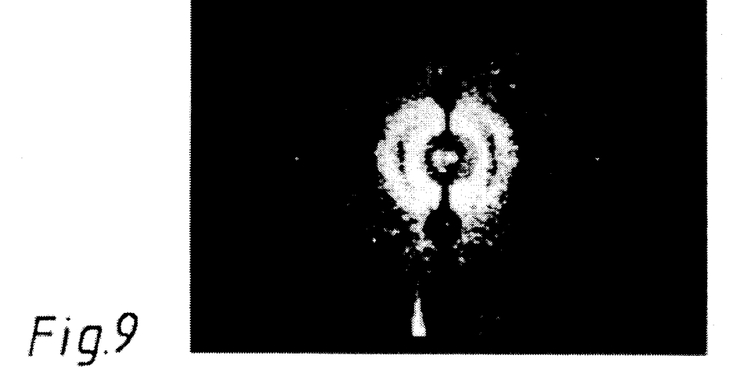
FIG. 9 shows the collected image of light scattered from a 1 micron polystyrene sphere between 30° and 140°.
Figure 10:
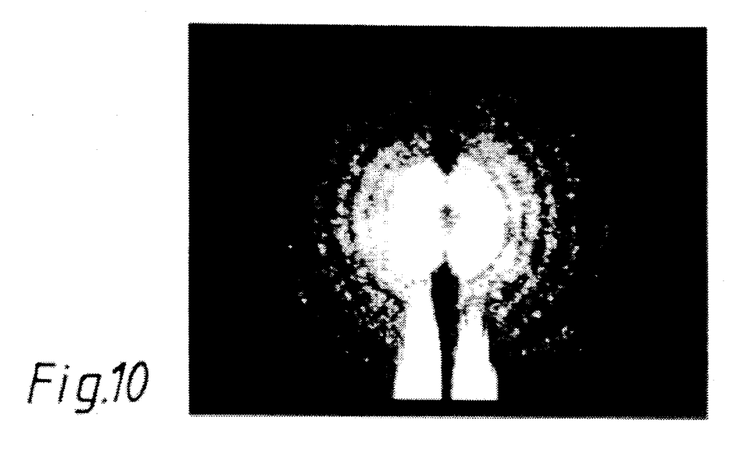
FIG. 10 shows the collected image of light scattered from a water droplet between 30° and 140°.
Figure 11:
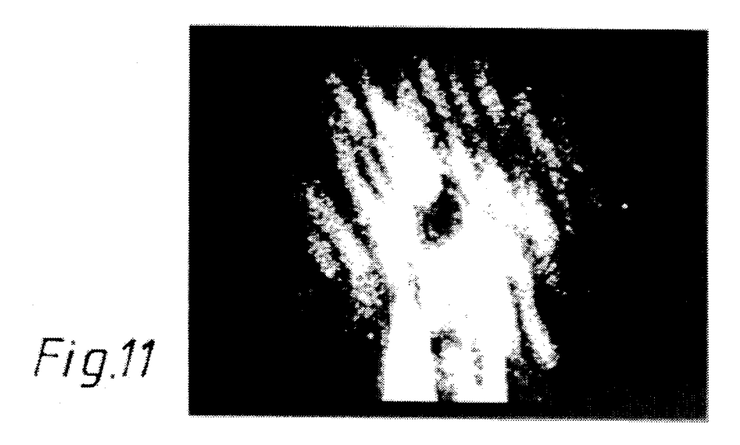
FIG. 11 shows the collected image of light scattered from an arbitrary airborne particle between 5° and 30°.

FIGS. 9, 10 and 11 show some images taken with the present system. The laser has a linearly polarized output so the scattering profiles are different in different scattering planes. This is because the scattering profile in any plane is dependent on the parallel and perpendicular components of the polarization of the incident beam, which are different fop each plane. The images from polystyrene spheres, water droplets and laboratory air have been captured. The images exhibit a grainy nature, especially at larger scattering angles, which is due to the small number of photons being scattered during the time the particle is in the beam. Each grain on the image corresponds to an individual photon incident on the faceplate of the image intensifier.

The images show spatial scattering profiles from approximately 30° around the central shadow region to approximately 141° around the edge of the pattern limit. The central shadow region is caused by the hole in the ellipsoidal reflector and its size varies depending on particle position in the scattering volume as predicted by the ray tracing package. The uncertainty in the scattering angle limits is because the system has not yet been calibrated to take into account changes in particle position, and it is known that the instrument is very sensitive to changes in particle position, particularly at small scattering angles.

The other shadow regions are caused by the inlet and outlet tubes 26, 27. The almost circular portions are caused by the ends of tubes 26, 27 intercepting light before it reaches the ellipsoidal reflector 17, the narrow portions ape caused by the sides of the tubes 26, 27 intercepting light after it has been reflected by the reflector 17. The 90° scattering angle is a circle whose circumference intercepts the centres of the circular shadow regions.

FIG. 9 shows a result from a 1 micron diameter polystyrene latex sphere. Concentric rings of scattering maxima and minima can be seen, which is consistent with the theory of scattering from spheres.

There is a good qualitative agreement between the image and theoretical predictions. In particular, it can be seen that the minimum which occurs at an angle of approximately 70° in the horizontal plane disappears in the vertical plane, which agrees with theoretical predictions. The scatter angles at which the maxima and minima occur are also in good agreement.

Simulations with 2.95 micron and 4.3 micron diameter spheres have also been carried out with similar correlation, although the high periodicity of the fringes and the non-linear nature of the experimental data make quantitative comparison at this stage more complex.

FIG. 10 shows a typical result from a water droplet generated using a water spray, with scattering between 30° and 140°. Since the spray generates a wide droplet size distribution, the diameters of the individual droplets creating the scattering profiles are not known. Simulations of scattering profiles from 2 micron and 2.5 micron diameter spherical water droplets have been carried out and these show that relatively more light is scattered in the 90° to 1400 angular range than is the case with polystyrene spheres. This can also be observed in the experimental data.

With the camera 36 positioned to capture small scattering angle data from 5° to 30°, the laser 10 was fitted with a 22% transmission broadband neutral density filter on its output to reduce the beam intensity 11, because without this, the amount of scattered light is such that the ccd array is saturated, and the image is normally completely white for droplets of the size range generated.

FIG. 11 shows an image taken when the instrument is operated with the inlet open to the atmosphere in the laboratory.

To summarise, the instrument possesses, inter alia, the capability of resolving diffraction maxima and minima with particles in the approximate size range (1–10) microns. The lower limit is governed by the number of scattered photons, which varies approximately in proportion to the fourth power of the diameter of the particle for particles of this size, and therefore changes by several orders of magnitude in the size range of interest. The lower limit could be reduced by using a more powerful laser but this would cause camera saturation problems with larger particles. The upper limit is caused by the number and closeness of the scattering maxima and minima and could be increased by using a camera with a higher resolution ccd array and redesigned instrument optics.

The nature of the ellipsoidal reflector 17 causes scattering angles below approximately 70° to be compressed into a relatively small area on the ccd array, and therefore detailed examination of this region could be facilitated by redesigning the lens system to expand this region, at the expense of losing scattering information at larger angles. The instrument would readily accommodate such changes.

With the use of a reflector 17 to collect light over a large solid angle, in combination with a lens system 34 which produces an image at the camera imaging plane largely insensitive to the particle's position within a column, and without any intermediate collecting lenses (For which it would be necessary to provide a transformation to correct for positional sensitivity introduced by such lenses), the instrument successfully images light scattered from individual particles even at small angles, without significant distortion.

The instrument still of course has some sensitivity to changes in particle position in the scattering volume, especially at small scattering angles. While this is a disadvantage when calculating the angles where diffraction maxima and minima occur, it is possible to take this into account by observing the size of the central shadow region. There will, however, always be some uncertainty in the calculations, especially at small angles.

The apparatus can also be exploited to determine the orientation of particles as they traverse the airflow between the inlet and outlet tubes 26, 27. The two tubes can be moved in relation to the laser beam 11, which effectively enables the scattering volume to be moved to different positions of the airflow across the gap. The distance between the tubes can also be changed so that airflows of different lengths can be investigated, and an investigation of the aligning effects of an electrostatic field can be carried out by putting a voltage on the outlet tube, which is electrically isolated from the rest of the instrument.

Although it is not possible to trace one particle across the complete airflow, it is possible to determine whether there is any preferred orientation of particles at any particular position in the airflow, and if so, whether this orientation changes as the particle moves with the flow.

From an investigation of the aerodynamics it should be possible to design a particle delivery system which ensures an almost constant orientation. This is seen to be a requirement in a practical instrument capable of shape discrimination since the number of detectors could be much less than on the research instrument of FIG. 2, and changes in orientation would almost certainly produce an incorrect shape result.

The apparatus could also be used to investigate the deformation of liquid droplets as they traverse the airflow. If any deformation can be detected, it may be possible to differentiate between solid spheres and droplets.

Droplets of known size would be generated using an aerosol generator, and experiments performed with liquids of different viscosities recording scattering profiles as droplets traverse the gap between inlet and outlet tubes.

One could then determine if there is any elongation or relaxation of droplets due to shear forces in the airflow across the gap, which would cause a non-spherical scattering profile. From the scattering profiles already obtained from water droplets, it is expected that any non-spherical scattering profile due to deformation will be small, and detection will almost certainly require computer analysis. Appropriate algorithms would detect deformations once the scattering profiles have been obtained.

Theoretical modelling of the aerodynamics of the particle delivery tube system can also be used, and compared with the experimental results. It should be possible then to determine an optimum delivery system so that droplets can be discriminated from solid spheres and non-spherical particles.

Although the apparatus has been used so far with aerosols in air or other gas, the apparatus could be used to detect characteristics of particles supported in a fluid or liquid medium, such as a colloidal suspension, with minor modifications to the chamber and optics. The detailed design of the optical and electrical components could also of course differ; for example, ccd arrays even as low as 32×32 pixels would be feasible, and the array could be of any regular or irregular shape.

It will be realised that, whilst the above described instrument has been described as having a camera 36 positioned usually to receive the greater percentage of scattered radiation and using the photomultiplier tube 25 as part of the camera trigger device, with the alternative of reversing these positions, it would in fact be possible to position cameras in both these positions, and to use the information from both. This would need some form of triggering device which might, for example, be a photomultiplier tube 25 to which some portion of the scattered light is diverted.

It will also be realised that the image intensifier 34 may not always be necessary, and that the imaging screen on which the image falls may, for example, be that of the camera 36.

What is claimed is:

1. Apparatus for analysis of individual particle characteristics from an aerosol or other suspension of particles in a particle stream, said apparatus including:

a scattering chamber including an optical system having an ellipsoidal reflector with an orifice therein leading to a rear chamber;

a monochromatic light source adapted to transmit a collimated beam of light along a main axis of the reflector;

means for directing said particle stream in a stream of finite thickness containing said particles through the beam of light at substantially a main focus of the reflector;

an optical system comprising a means for collecting scattered light from a solid angle of at least 3π around a region where the particle stream crosses the light beam;

a detector having a two dimensional array of a multitude of sensors for forming an image from light scattered from a particle in the particle stream and collected by the optical system;

and a data processor for comparing parameters of the image with parameters stored in a memory to determine a characteristic of the particle;

the detector is associated with an imaging screen positioned behind a secondary focus of the reflector said optical system, said light source, and said means for directing, in combination, comprising a means for providing monotonically ordered scattered rays of light at said imaging screen such that, whatever part of the finite thickness of the particle stream occupied by the particle when it passes through the beam of light, rays of light scattered from the particle and imaged thereon by the optical system are monotonically ordered with respect to the angle of scattering of the rays from the particle so that the image recorded on the imaging screen is substantially independent of position of the particle in the particle stream.

2. Apparatus as claimed in claim 1 wherein the detector is a charged couple device (ccd) video camera.

3. Apparatus as claimed in claim 1 wherein the imaging screen is an image intensifier.

4. Apparatus as claimed in claim 1 further including trigger means for triggering the detector to store the image.

5. Apparatus as claimed in claim 4 wherein the trigger means includes sensor means for sensing scattered light not collected by the optical system and thereby determining presence of a particle in the beam of light.

6. Apparatus as claimed in claim 5 wherein the sensor means comprises a photomultiplier tube onto which is focussed scattered rays which pass through the orifice in the optical system into the rear chamber.

7. Apparatus as claimed in claims 4 wherein the trigger means includes a controller having an output to the detector.

8. Apparatus as claimed in claim 4 wherein the trigger means include means for triggering the detector only when a single particle is in the beam.

9. Apparatus as claimed in claim 1 wherein the rear chamber contains a second video camera to record scattered light not collected by the optical means.

10. Apparatus as claimed in claim 1 wherein the parameters compared relate to entire images.

11. Apparatus as claimed in claims 1 wherein the parameters compared relate to parts of images.

12. Apparatus as claimed in claim 1 wherein the parameters compared relate to resolving diffraction or interference maxima and minima.

13. Apparatus as claimed in claim 1 wherein the multitude of sensors are arrayed in a configuration of substantially 32 by 32 pixels.

14. Apparatus as claimed in claim 1 wherein the multitude of sensors are arrayed in a shape according to an expected image.

15. A method as claimed in claim 1 wherein said particle stream is an gaseous particle stream.

16. A method of analysing individual particle characteristics from an aerosol or other suspension of particles includes the steps of:

directing a particle stream of finite thickness containing said particles through a scattering chamber;

the scattering chamber including an optical system having an ellipsoidal reflector having a main focus and a secondary focus and with an orifice therein leading to a rear chamber;

a monochromatic light source adapted to transmit a collimated beam of light along a main axis of the reflector;

means for directing the particle stream through the beam of light at substantially the main focus of the reflector;

collecting by means of an optical system scattered light from a solid angle of at least 3π around a region where the particle stream crosses the light beam;

the scattering chamber is associated with a detector having a two dimensional array of a multitude of sensors arranged to form an image from light scattered from a particle in the particle stream and collected by the optical system;

recording said image in said detector and passing information to a data processor, the data processor being adapted to compare parameters of the image with parameters stored in a memory to determine the nature of the particle;

the detector is associated with an imaging screen positioned behind the secondary focus of the reflector wherein the directing step includes locating said scattering chamber relative to said imaging screen such that, whatever part of the finite thickness of the particle stream occupied by the particle when it passes through the beam of light, rays of light scattered from the particle and imaged thereon by the optical system are monotonically ordered with respect to the angle of scattering of the rays from the particle so that the image recorded on the imaging screen is substantially independent of position of the particle in the particle stream.

17. A method as claimed in claim 16 wherein the detector is triggered to store an image by a triggering system including sensor means for sensing scattered light not collected by the optical system.

18. A method as claimed in claim 16 wherein said particle stream is an gaseous particle stream.

* * * * *